United States Patent [19]

Rosenberg et al.

[11] Patent Number: 5,333,717

[45] Date of Patent: Aug. 2, 1994

[54] APPARATUS FOR SEPARATING CUVETTES

[75] Inventors: Burkard Rosenberg, Horw; Gottlieb Schacher, Ebikon, both of Switzerland

[73] Assignee: Hoffmann-La Roche Inc., Nutley, N.J.

[21] Appl. No.: 49,754

[22] Filed: Apr. 19, 1993

[30] Foreign Application Priority Data

Apr. 30, 1992 [CH] Switzerland .......................... 1391/92

[51] Int. Cl.⁵ ............................................ B65G 47/24
[52] U.S. Cl. .................................... 198/389; 198/392
[58] Field of Search ........................ 198/389, 392, 373

[56] References Cited

U.S. PATENT DOCUMENTS

| 2,025,273 | 2/1935 | Dellaree . | |
|---|---|---|---|
| 3,658,207 | 4/1972 | Schultz | 198/392 X |
| 3,907,099 | 9/1975 | Smith | 198/389 |
| 4,128,159 | 12/1978 | Pataki | 198/389 |
| 4,238,023 | 12/1980 | Millar et al. | 198/392 X |
| 4,306,649 | 12/1981 | Berge . | |
| 4,312,438 | 1/1982 | Vatsvog | 198/392 |
| 4,453,626 | 6/1984 | Roberts et al. | 198/392 X |
| 4,610,345 | 9/1986 | Spreen et al. | 198/392 |

FOREIGN PATENT DOCUMENTS

| 2532763 | 7/1975 | Fed. Rep. of Germany . | |
| 0075520 | 3/1990 | Japan | 198/389 |

OTHER PUBLICATIONS

Derwent Abstract No. H2247X/33 of DE 2 532 763, May 1976.

*Primary Examiner*—D. Glenn Dayoan
*Attorney, Agent, or Firm*—George M. Gould; George W. Johnston; Robert A. Silverman

[57] ABSTRACT

An apparatus for automatically separating cuvettes supplied in bulk form to an analytical instrument, the cuvettes being suitable for the performance of photometric measurements on samples contained in the cuvettes. To automatically separate cuvettes, the apparatus contains a receiving station for receiving the cuvettes in bulk form. It also includes a device for separating cuvettes, the device having an inlet through which disordered cuvettes can be supplied to the device, and an outlet through which individual cuvettes successively leave the device. A device is provided for conveying disordered cuvettes from the receiving station to the inlet of the device for separation of the cuvettes.

12 Claims, 10 Drawing Sheets

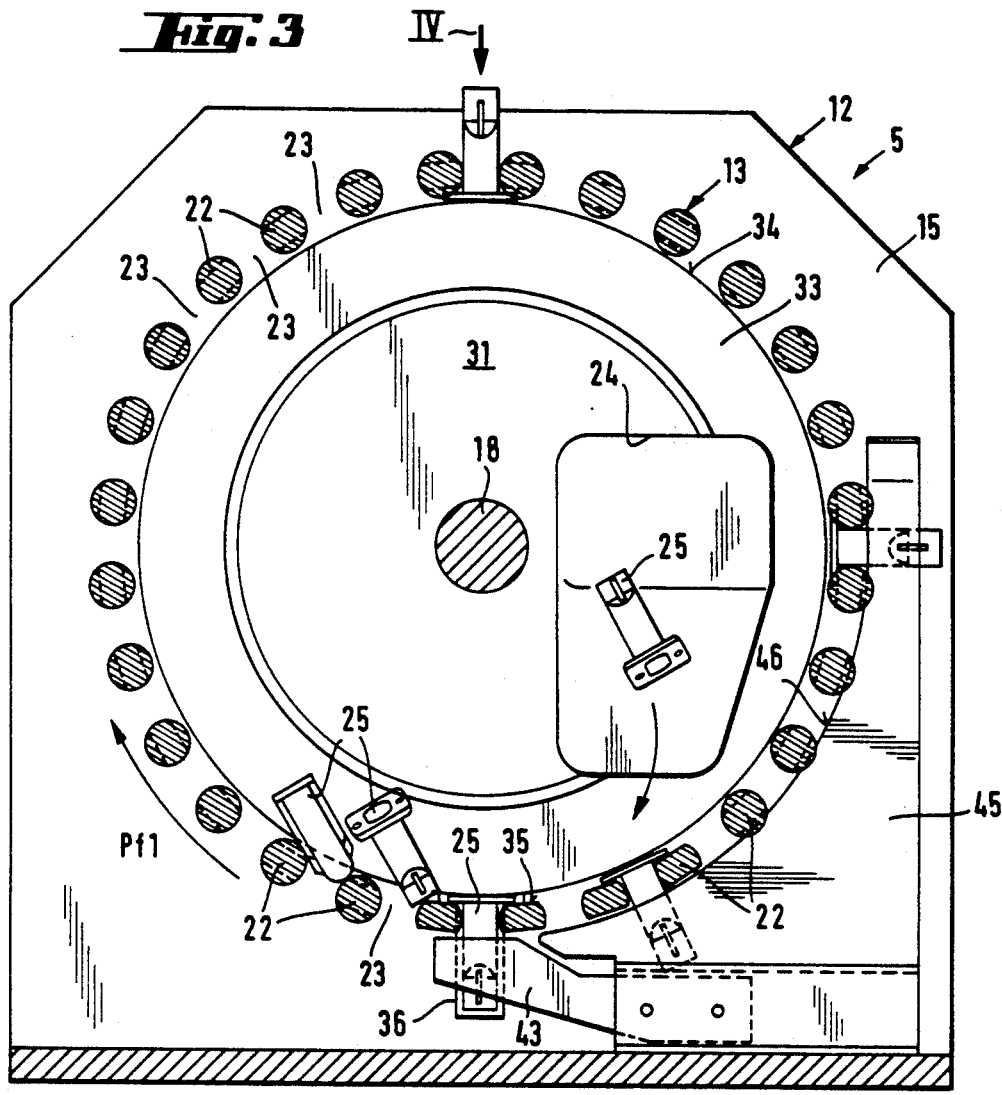
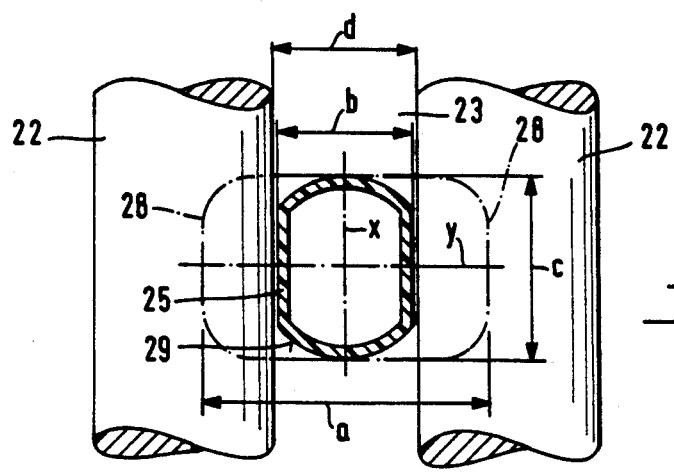

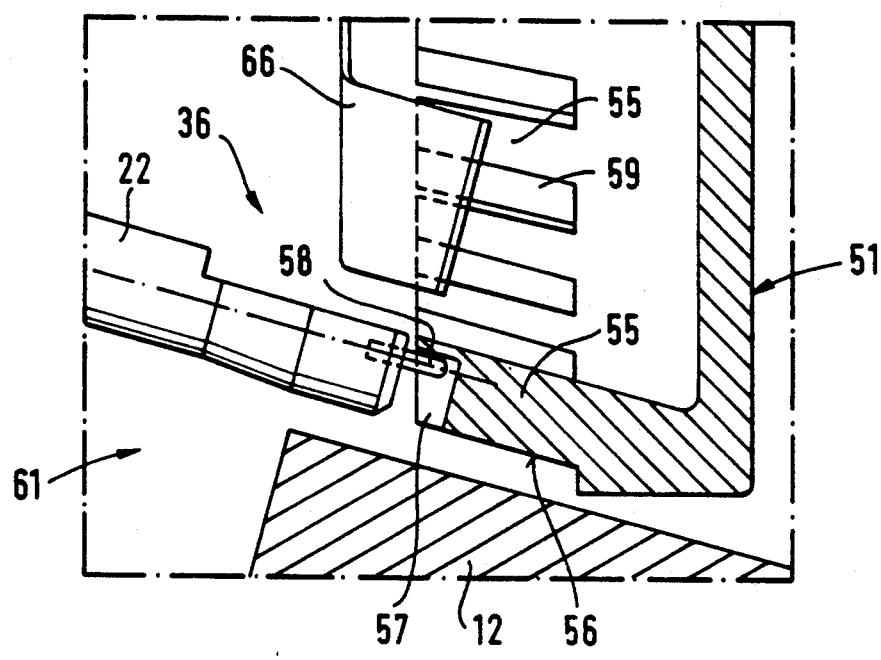
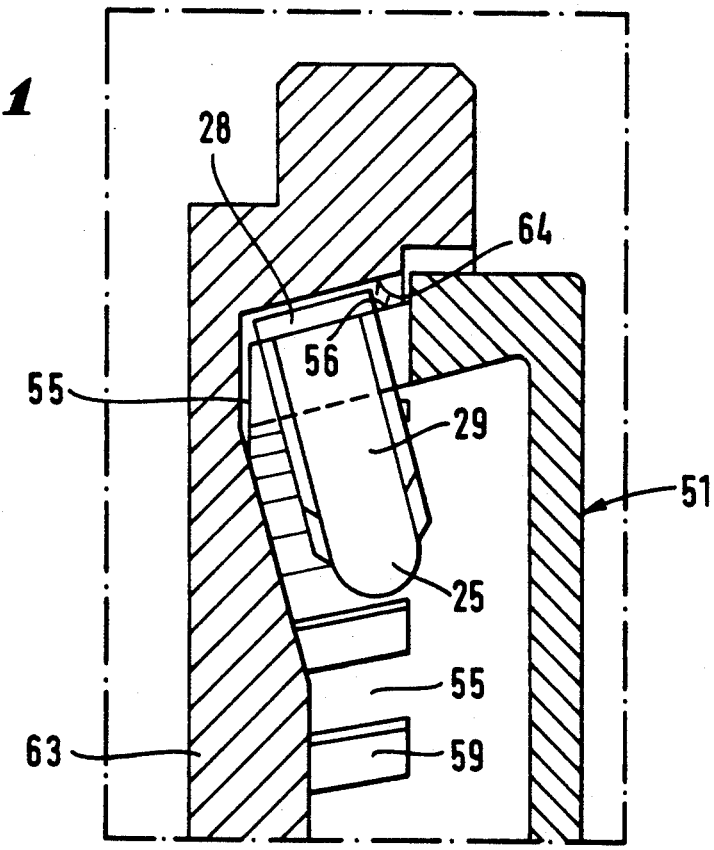

APPARATUS FOR SEPARATING CUVETTES

BACKGROUND OF THE INVENTION

1. Field of the Invention

The invention relates to an apparatus for separating cuvettes supplied in bulk form to an analytical instrument. The cuvettes are suitable for the performance of photometric measurements on samples in the cuvettes.

2. Description of the Invention

Automatic analytical instruments usually operate on the principle that analytical samples or parts thereof are placed in measurement cuvettes and then subjected to a series of processing steps such as adding (pipetting) reagents, mixing, incubation etc. the end of processing. The cuvettes containing the analytical samples are placed in a fixed sequence on a conveyor and travel through various processing stations. For batch processing (as is usual in the case of centrifugal analytical instruments), all measuring cuvettes usually are placed on a carrier (rotor) and subjected quasisimultaneously to the processing steps and photometric measurements. Analytical systems operating on these principles provide good service in large clinics and analytical centers where many samples have to be processed.

In view of the variety of possible analyses today and the medical requirements particularly in clinical chemistry, the conventional automatic analyzers for the throughput of large quantities of samples are insufficiently flexible to provide analytical profiles (full random access) specifically adapted to individual patients or clinical pictures.

To obtain the desired high flexibility, a reliable system must be provided in the analytical system for conveying and processing individual measuring cuvettes.

Since the number of measuring cuvettes to be processed is very large, it is desirable to load the instrument with empty cuvettes in bulk form. Before the present invention, the known analytical instruments could not automatically separate the cuvettes. Following loading, the cuvettes can be automatically separated in the instrument in accordance with the invention and can be conveyed by a suitable means for use in the aforementioned analytical procedure.

SUMMARY OF THE INVENTION

The invention concerns a device for separating cuvettes which are supplied in bulk to an analytic instrument. Each cuvette is made in one piece from light-transmitting plastic and has a tubular body with two plane-parallel walls. Each plane-parallel wall has a flange attachment which extends outwards and at right angles to the plane-parallel walls. The flange attachments of the two plane-parallel walls are symmetrical with one another relative to the longitudinal axis of the cuvette.

The apparatus includes a receiving station for receiving cuvettes in bulk form. There also is included a device for separating the disordered cuvettes, the device having an inlet through which the disordered cuvettes are conducted into the device and an outlet through which the individual, oriented cuvettes successively leave the device. Also, means are provided for conveying disordered cuvettes from the receiving station to the inlet of the device for separating the cuvettes.

The device for separating disordered cuvettes contains the following components. A fixed plate is mounted on a base plate and disposed at an angle to a vertical line. A bearing rod is mounted on the fixed plate and disposed at right angles thereto. A rotatable disc is rotatably mounted on the bearing rod and disposed parallel to the fixed plate. A cylindrical arrangement of equal-sized cylindrical rods is secured to the rotatable disc. The rods are equally spaced apart around a circle concentric with the bearing rod. The rods are aligned parallel to the bearing rod and, like the bearing rod, are inclined at an angle to a horizontal line. One end of each rod is permanently connected to the rotatable disc whereas the other end of the rod is free and is separated from the fixed plate by a predetermined gap to form a cage-like structure. The distance between adjacent rods is just sufficient for the body of a cuvette to enter between the rods when the plane-parallel walls of the cuvette are parallel to the longitudinal axis of the rods. However, the gap is not so large as to permit the cuvettes to fall completely through and from the cage-like structure.

Motor-driven means is provided for rotating the rotatable disc preferably at a constant speed. A fixed annular disc is mounted on the fixed plate and has a central aperture for disposition of the bearing rod. The peripheral edge of the disc is positioned inside the cylindrical arrangement of rods, and the distance between the rods and the edge of the fixed annular disc is slightly greater than the thickness of the flange attachments on the cuvettes. A first opening is defined in the fixed plate, at a position above the bottom edge of the fixed annular disc. The opening serves as an inlet for inserting disordered cuvettes into the cage-like structure formed by the fixed plate, the arrangement of rods and the rotatable disc.

Further, the device for separating disordered cuvettes preferably contains the following additional components. A second opening is defined in the fixed plate, at the top edge of the fixed annular disc. The opening serves as an outlet for discharging individual cuvettes when their flange attachments come to rest between the arrangement of rods and the peripheral edge of the fixed annular disc during rotation of the cage-like structure. There also is included means for delivering individual cuvettes through the second opening in the fixed plate, when the cuvette is immediately in front of the second opening during rotation of the cage-like structure.

When the cuvettes are separated in accordance with the previously described invention, the cuvette walls are protected from scratching and the cuvettes are prevented from jamming. Additionally, the separated cuvettes are delivered in a predetermined position and are made available at the speed required by the conveyor in the automatic analyzer.

DESCRIPTION OF THE DRAWINGS

Embodiments of the invention will be described with reference to the accompanying drawings, in which:

FIG. 3 is a cross-section along line III—III in FIG. 2;

FIG. 4 is a view (taken in the direction of arrow IV in FIG. 3) of two rods of a rotor drum according to FIG. 3, with a diagrammatically indicated cuvette;

FIG. 10 is a section along line X—X in FIG. 9; and

FIGS. 11 to 13 are partial views taken in a direction along arrows XI to XIII in FIG. 9.

DETAILED DESCRIPTION OF THE PREFERRED EMBODIMENTS

Figure 1:
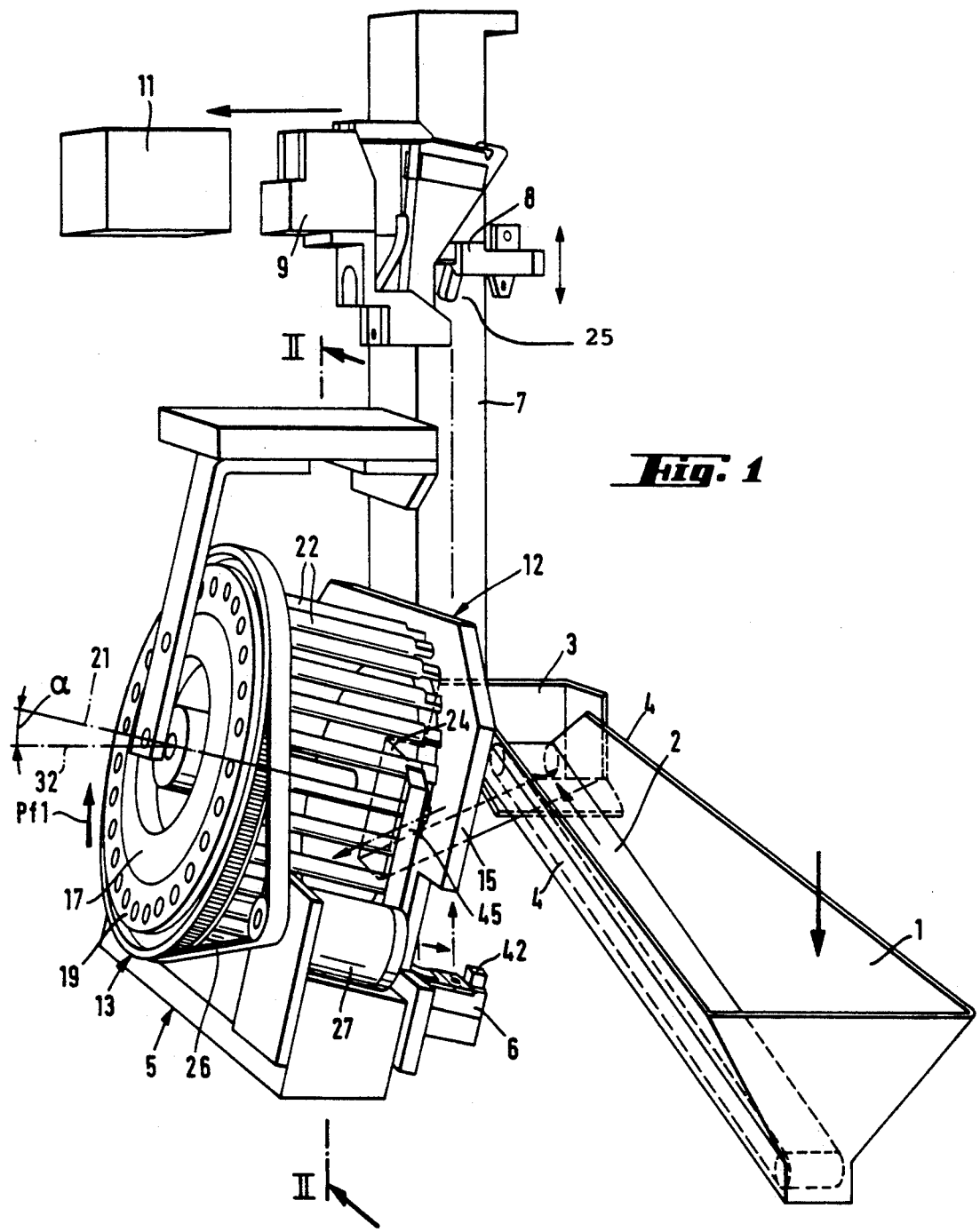
FIG. 1 shows an apparatus according to the invention in perspective view.

The present invention concerns an apparatus for separating a plurality of cuvettes, which are supplied in bulk form to an analytical instrument. The cuvettes are suitable for the performance of photometric measurements on samples contained in the cuvettes. Each cuvette is made from a one-piece light transmitting plastic and has a tubular body with two plane-parallel walls. Each plane-parallel wall has a flange attachment which extends outwardly and at right angles to the plane-parallel walls. The flange attachments of the two plane-parallel walls are symmetrical with one another relative to the longitudinal axis of the cuvette.

The apparatus comprises a receiving station for receiving cuvettes in bulk form. It also includes a device for separating the cuvettes, which device has an inlet through which cuvettes are conducted into the device and an outlet through which individual cuvettes successively leave the device. Means also are provided for conveying disordered cuvettes from the receiving station to the inlet of the device.

More particularly, the device for separating the cuvettes includes a base plate, and a fixed plate mounted on the base plate and disposed at a predetermined angle to a vertical line. The device further includes a bearing rod which is mounted on the fixed plate and disposed on right angles thereto. The bearing rod also is inclined at a predetermined angle to a horizontal line. A rotatable disc is rotatably secured or mounted on the bearing rod and disposed parallel to the fixed plate. The disc also has a peripheral edge. A cylindrical arrangement of equally size cylindrical rods having two ends are secured to the rotatable disc. The rods are equally spaced apart from each other around a circumference which is concentric with the axis of the bearing rod. The rods are aligned parallel to the bearing rod and inclined at the same angle to a horizontal line as is the bearing rod. One end of each cylindrical rod is permanently secured to the rotatable disc and the other end of the rod is free and separated from the fixed plate by a predetermined distance or gap. The distance between adjacent cylindrical rods is sufficient for the tubular body of the cuvette to enter between the adjacent rods when the plane-parallel walls are parallel to the longitudinal axis of the rods but not so large as to let the cuvettes pass completely there through. The fixed plate, cylindrical rods and rotatable disc form a cage-like structure for securing the disoriented cuvettes therein.

The device for separating the cuvettes also includes motor-driven means for rotating the rotatable disc at a predetermined speed. It also includes a fixed annular disc mounted on the fixed plate and has a central aperture for receiving the bearing rod. The peripheral edge of the disc is configured and dimensioned to be within or inside the circumference of the arrangement of cylindrical rods. The distance between the cylindrical rods and the peripheral edge of the fixed annular disc is slightly greater than the thickness of the flange attachments on the cuvettes. Lastly, there is provided a first opening on the fixed plate, which is positioned above the lowest portion of the fixed annular disc with respect to the vertical line. This opening serves as an inlet for inserting the disordered cuvettes into the cage-like structure.

FIG. 1 shows a cuvette hopper 1 which can hold disordered cuvettes in the form of a loose heap of (e.g., 3000) cuvettes. The disordered cuvettes are transferred at a metered rate from the hopper 1 to a supply funnel 3 of a cuvette-separating device 5 by an upwardly sloping conveyor belt 2, which is disposed at the base of a channel formed by side walls 4. The belt is continuously or discontinuously drivable, depending on the required volume of cuvettes.

The cuvette-separating device 5 is preferably an aligning and separating device in which the disordered cuvettes, supplied at random, are moved into a single possible position and the cuvettes, which are aligned by the device into a predetermined position, are separated from the disordered cuvettes. When required, the correctly-positioned cuvettes are ejected from the aligning and separating device 5 and transferred to a store or storage device 6.

One cuvette at a time can be transferred from the store 6 by a gripper 8 on a cuvette hoist 7, via a delivery device 9 to a working plane of a working station 11, shown diagrammatically as a block. If the working plane is approximately in the plane of access of the cuvette 25 at the outlet of the store 6, a hoist is not necessary. In that case it is sufficiently to provide a suitable gripper for conveying the cuvette to the work station.

FIGS. 2 to 6 show an aligning and separating device 5 and they illustrate the operation of the device. In the figures, structural components not necessary for understanding have been omitted for simplicity.

The aligning and separating device 5 substantially comprises a stator 12 and a rotor 13. The stator 12 has a bearing block 14 which supports a stator plate 15. the stator plate 15 closes one end of the rotor 13. The rotor 13 is rotatably mounted via a ball bearing 16 on a bearing disc 17, which is rigidly connected to the bearing block 14 by a bearing rod 18 at a predetermined distance from the stator plate 15. The bearing rod 18 is disposed at right angles to the stator plate 15 and to the bearing disc 17. The bearing disc therefore is parallel to the stator plate 15. The bearing disc 17 co-operates with a rotatable disc 19 to close the rotor 13 at the end opposite the stator plate 15. The cylindrical outer jacket of the rotor 13 is formed by rods 22, preferably having a round cross-section, and projecting at right angles from the disc 19, parallel to the axis of rotation 21 of the rotor and in the direction of the stator plate 15. The rod diameter and the angular distances between rods 22 on their common pitch circle are dimensional and adapted to one another so as to obtain spaces 23 having a defined width b (FIG. 4) and aligned parallel to the axis of rotation 21.

One end of each rod 22 is permanently connected to the disc 19. The other end of each rod 22 is free and is separated by a predetermined gap from the stator plate 15.

The rods 22 are aligned parallel to the bearing rod 18 and similarly are inclined at angle $\alpha$ to a horizontal line 32. Since the bearing rod 18 is perpendicular to the stator plate 15, this plate is inclined an angle $\alpha$ to a vertical line, i.e. a line perpendicular to horizontal line 32.

Cuvettes 25 can be transferred to the interior of the cage-like rotor 13 through a supply opening 24 in the stator plate 15, which is connected to a funnel 3 (FIGS. 1 and 3).

The rotor 13 is connected to the drive motor 27 by a belt 26 which peripherally engages the disc 19 (FIG. 1). During operation, the rotor is continuously driven in rotation at a constant speed. The speed of the rotor is preferably between 8 and 15 revolutions per minute. A speed of about 11 revolutions per minute is preferred.

The need to align the cuvettes 25 is due to the asymmetry of each cuvette relative to the x and y axis (FIG.4). According to the invention, the asymmetry is advantageously used to align the cuvettes 25 with respect to the distance between rods 22.

An aforementioned cuvette 25, (FIGS. 4 & 6) in its edge region on the opening side, has two diametrically opposite flange attachments 28 facilitating transport of the cuvette 25, the flange attachments having a width a in the y direction which exceeds the dimension b of the cuvette tube 29 in the y direction. The dimension c of the tube section 29 of cuvette 25 in the x dimension is equal to the dimension of the flange attachments 28 in the x direction. The dimension b of the cuvette tube 29 is less than c. The internal distance d between two adjacent rods 22 is slightly greater than b but appreciably less than c.

Consequently, the cuvette tube 29 cannot pass between two rods 22 unless its x axis is parallel to the axis or rotation 21 of the rotor. The flange attachments 28 abut the rods 22 at the top, thus preventing the cuvettes 25 from falling out of the cage-like interior 31 of the rotor.

As shown in FIG. 3, the supply opening 24 in the stator plate 15 is offset relative to the axis of rotation 21 of the rotor 13, so that the cuvettes 25 for transferring to the rotor interior 31 reach the initially descending region, allowing for the rotation (arrow Pf1) and the resulting vertical change in the position of rods 22. As a result of the rotation of the rotor drum 13 (arrow Pf1), the cuvettes 25 reach the lowest region of the rotor drum 13, and some cuvettes 25 through gravity, have their tube in the correct position to permit passage of the tube between the rods 22. The as yet unaligned cuvettes 25 are then entrained into the rising region of the motor drum 13, thus rotating them against gravity and ultimately aligning the cuvette 25 (FIG. 3).

Figure 2:
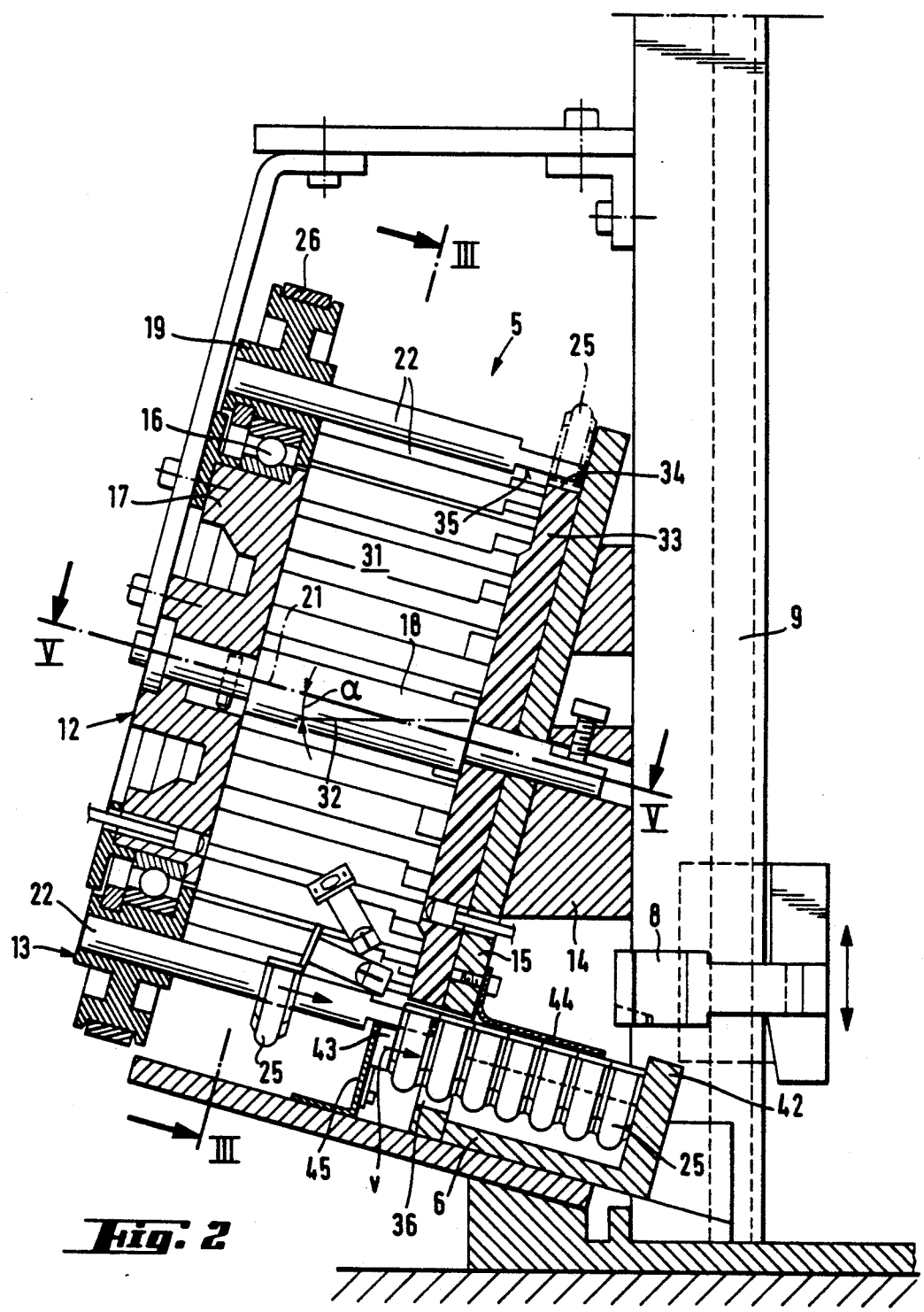
FIG. 2 is a longitudinal section along line II—II in FIG. 1.
Figure 5:
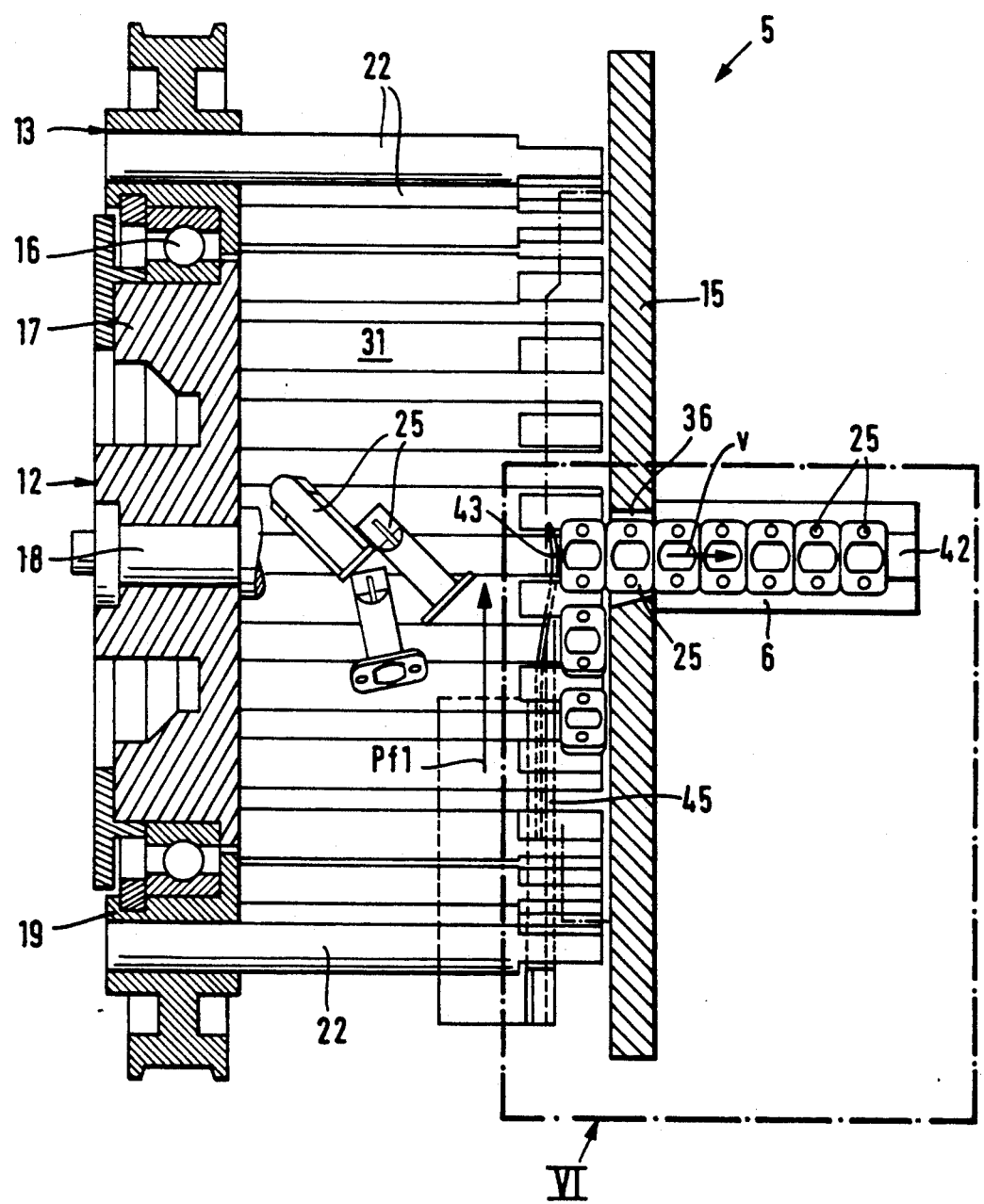
FIG. 5 is a section along line V—V in FIG. 2.
Figure 6:
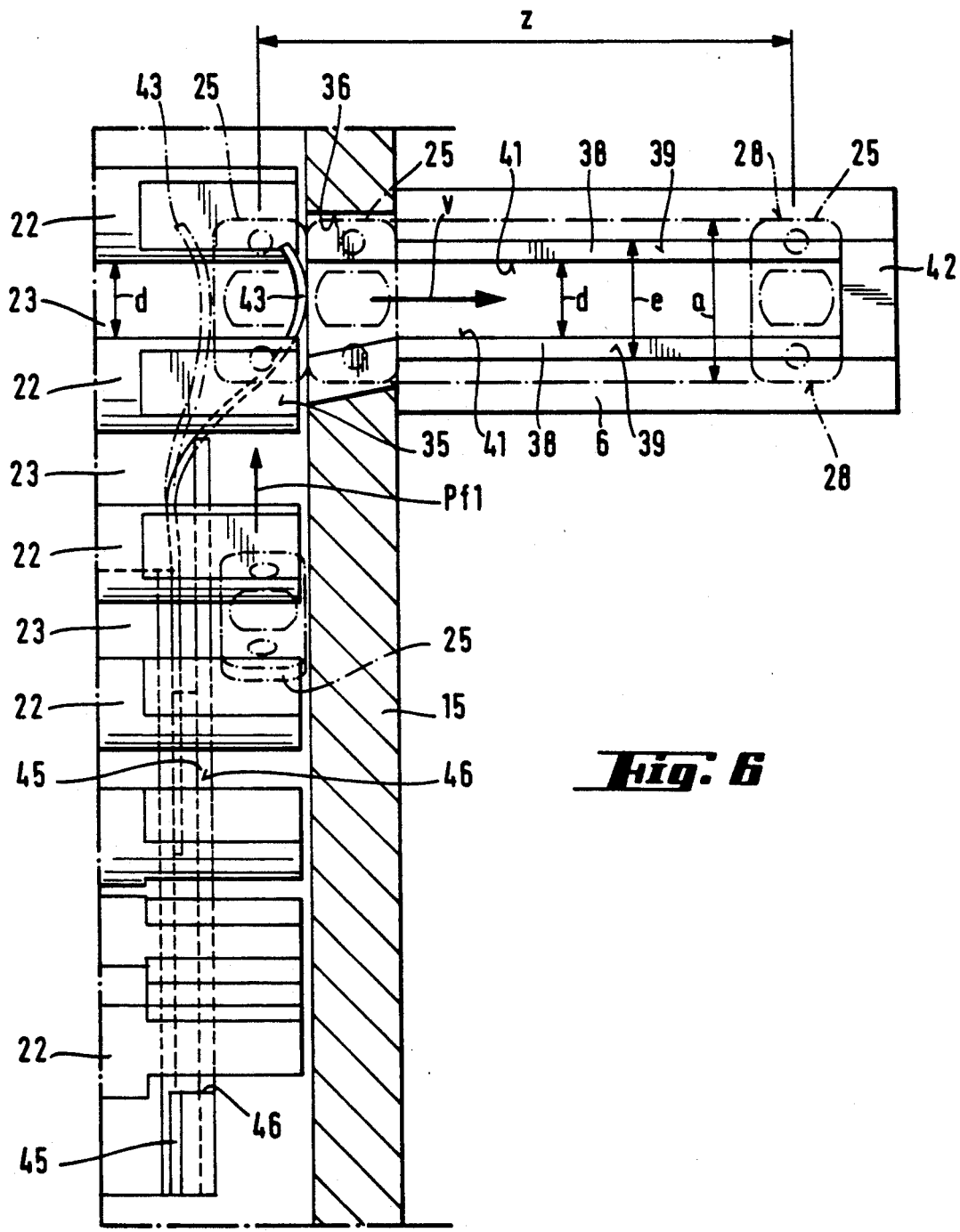
FIG. 6 is a larger-scale portion (taken in the area of box VI) of FIG. 5.
Figure 7:
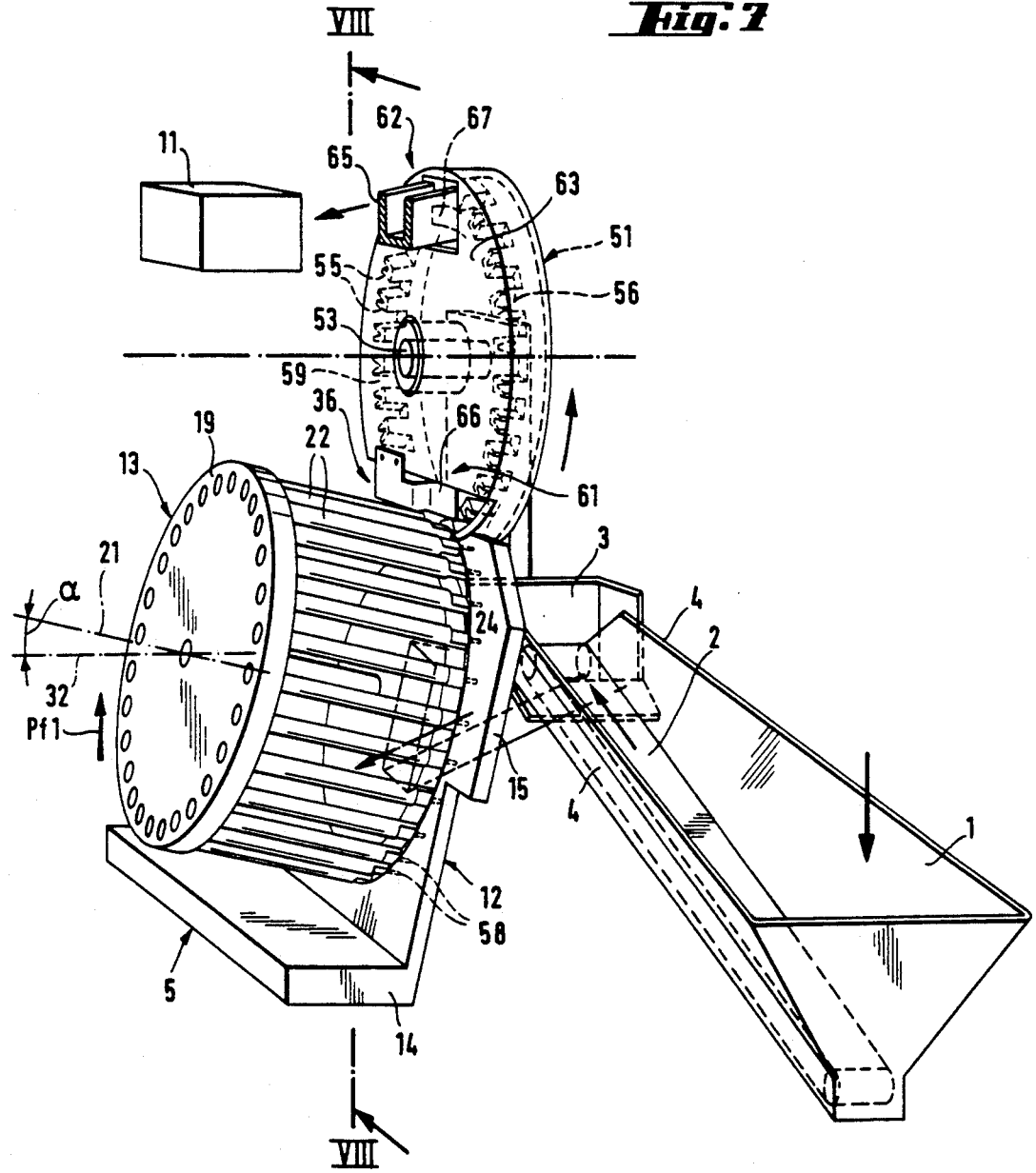
FIG. 7 is another embodiment of the apparatus according to the invention in perspective view.

The axis of rotation 21 of the rotor is inclined to the horizontal 32 by an angle α so that aligned cuvettes 25, through gravity, can slide towards the stator plate 15 until they abut it (FIG. 2). The angle α is preferably between 10 and 20 degrees. An angle α=15 degrees is most preferred.

When the aligned cuvettes 25 abut the stator plate 15, the outer peripheral edge 34 of a guide disc 33 on the stator plate 15 overlaps the mouths or flanges of the cuvettes (FIGS. 2 and 3). The guide disc 33 has a central aperture for the bearing rod 18 and an opening (not shown in the drawings) coinciding with the supply opening 24 through the stator plate 15. The guide disc 33 is preferably made of polyoxymethylene (POM). As FIG. 3 shows, the distance between the rods 22 and the edge of the guide disc 33 is slightly greater than the thickness of the flange attachments on the cuvettes.

When the rotor 13 rotates further, the aligned cuvettes 25 reach the upper region. The outer peripheral edge 34 can retain the aligned cuvettes 25 against gravity because the cuvettes are retained in the upper region, so that the cuvettes 25 remain in the position between the rods 22. The axial extent or width of the peripheral edge 34 is chosen so that only one cuvette 25 is guided or retained. If, for example, two cuvettes 25 are successively aligned and present in a space 23 between two rods 22, only the cuvette 25 near the stator plate is held in the position. The second cuvette 25 loses its alignment and falls through gravity into the bottom region of the rotor 13.

Flat portions 35 on the ends of the rods 22 (on the same side as the stator plate) enhances the grip for the cuvette flanges 28.

In order to ensure that the cuvettes are treated gently during the aforementioned separating process, the rotor should have minimum mass. To this end, the rods 22 are preferably made of a light metal, (e.g., aluminum). To improve the sliding properties of the cuvettes on the rods 22, the rods also are preferably provided with a suitable coating. To this end, aluminum rods 22 are coated with nickel and Teflon (e.g., 30% nickel and 70% Teflon).

The aligned cuvettes 25, whose flanges 28 can be disposed between the peripheral edge 34 and the flat parts 35 of rods 22, can leave the interior 31 of the rotor only through a specially provided opening or window 36, and thus can be regarded as having been aligned and separated. These separated cuvettes 25 rotate with the rotor in the direction Pf1 and provide a supply from which individual cuvettes can be taken when needed.

Individual separated cuvettes 25 from the aforementioned supply can leave the rotor interior 31 through window 36 formed in the stator plate 15 and having a shape similar to that of the cuvettes 25. The cuvettes are moved forward and ejected (e.g., by a leaf spring 43 (FIG. 2)), which is configured and positioned to convey cuvettes 25 through the window 36 (FIGS. 2, 3, 5 and 6).

Cuvette store 6 is disposed in line with the window opening 36. The cuvettes 25 are guided by narrow vertical strips 38 (FIG. 6), which have an upper surface 39 on which the undersides of the cuvette flanges 28 slide. The cuvette tube 29 is guided by the inner surfaces 41 (spacing d) of the strips 38. An abutment 42 is provided on the ends of the strips 38 opposite the window 36. One cuvette 25 at a time comes against the abutment in the correct position, in a plane of access of a gripper 8, (e.g., on a cuvette hoist 7 (FIG. 1)). The position of the cuvette 25 in the plane of access is at a distance, determined by the construction, from the separated cuvette 25 in the cuvette supply (inside the rotor) (distance z in FIG. 6). Since the width e between the strips 38 is less than the flange width a, the gripper 8 can grip the ends of the flanges.

After a cuvette 25 have been taken from the store 6, the next cuvette can be positioned in the plane of axis of the gripper (FIGS. 2, 5, 6) by the leaf spring 43 (FIG. 3). The spring acts on a separated cuvette 25 in the supply in the rotor interior, the cuvette being in line with the window 36, and also acts on a row of cuvettes already in the store 6 and bridging the distance z (shown as force v in FIGS. 5 and 6).

The cuvettes 25 bridging the distance z in the store 6 are secured at the top by a leaf spring 44 which in turn is secured to the stator plate 15 (FIG. 2).

To prevent cuvettes 25 from jamming near the leaf spring 43, a partition 45 is provided between the separated cuvettes 25 in the store and the disordered (i.e., not yet aligned) cuvettes inside the drum 31 or the rotor 13. The partition extends over an angle of about 90° around the supply opening 24 in the stator plate 15 (FIG. 3).

The partition 45 is secured to the stator base and has a contour 46 which is configured and dimensioned to correspond to the outer diameter of the rotor.

The partition 45 is adapted to keep cuvettes 25 away from the leaf spring area when the cuvettes extend through the spaces 23 between the rods 22. The leaf spring 43 is secured to the partition 45.

The drive for rotating the rotor is continuous, irrespective of how many cuvettes are needed. One cuvette preferably is needed for example every six seconds.

It is only necessary to ensure that the rotor is filled with disordered cuvettes to a substantially constant level, which can be accomplished by adjusting the supply from the cuvette hopper. A skilled artisan would be familiar with suitable, (e.g., optical) monitoring devices for adjusting the supply of cuvettes to the rotor.

In the embodiment described above, the individual cuvettes 25 leave the interior of the rotor 31 of the aligning and separating device 5 through an outlet lying on the lower part of a guide disk 33. The cuvettes 25, which are delivered at this outlet, are transported by transport means containing a cuvette store 6, a gripper 8 and a delivery device 9.

A more preferred variant of the apparatus provided by the invention will be described with reference to FIGS. 7 to 13. In this variant the aforementioned transport means is replaced by a rotating wheel 51, and the outlet 36 of the aligning and separating device 5 is situated not on the lower part, but on the upper part of the guide disk 33.

Figure 8:
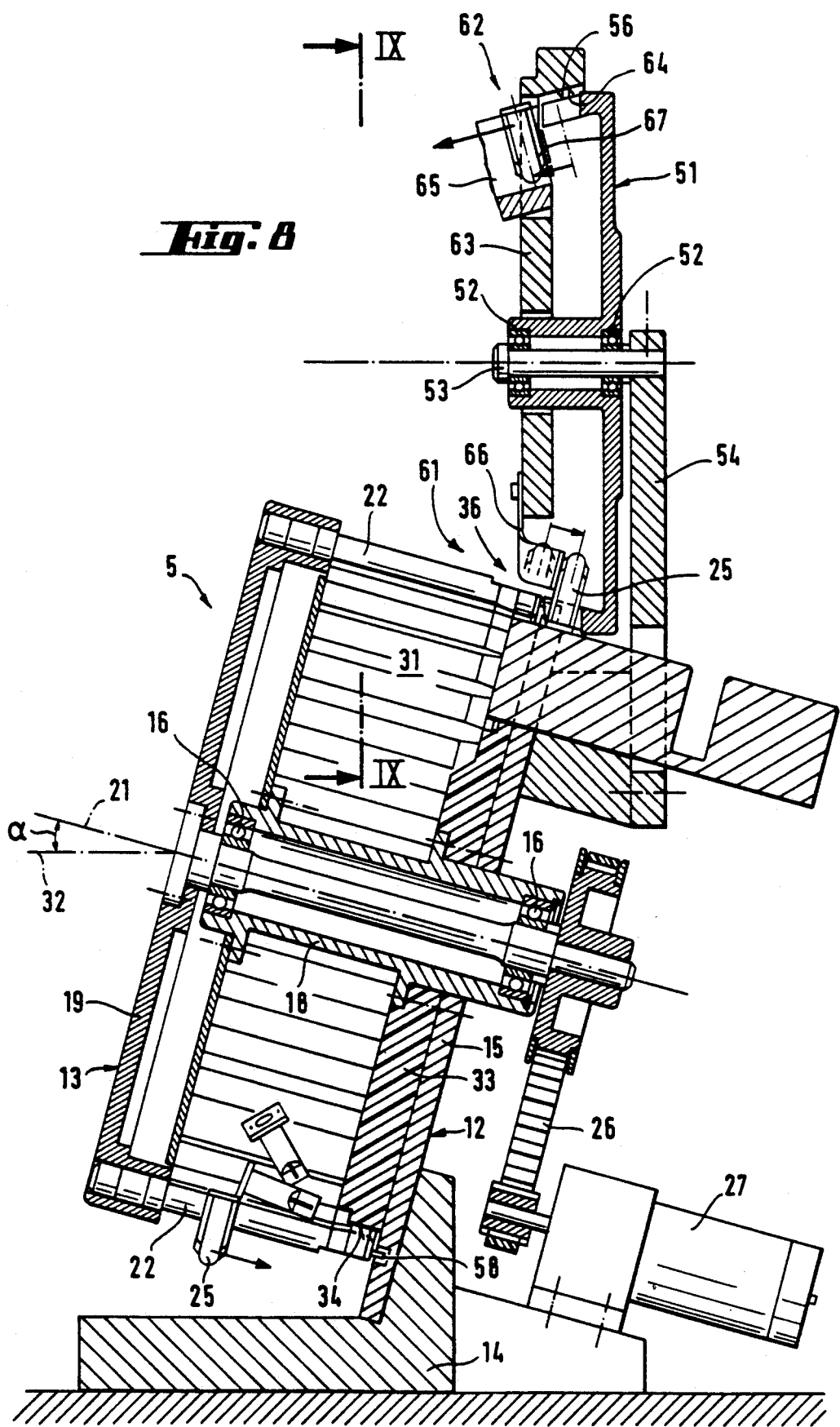
FIG. 8 is a longitudinal section along line VIII—VIII in FIG. 7.
Figure 9:
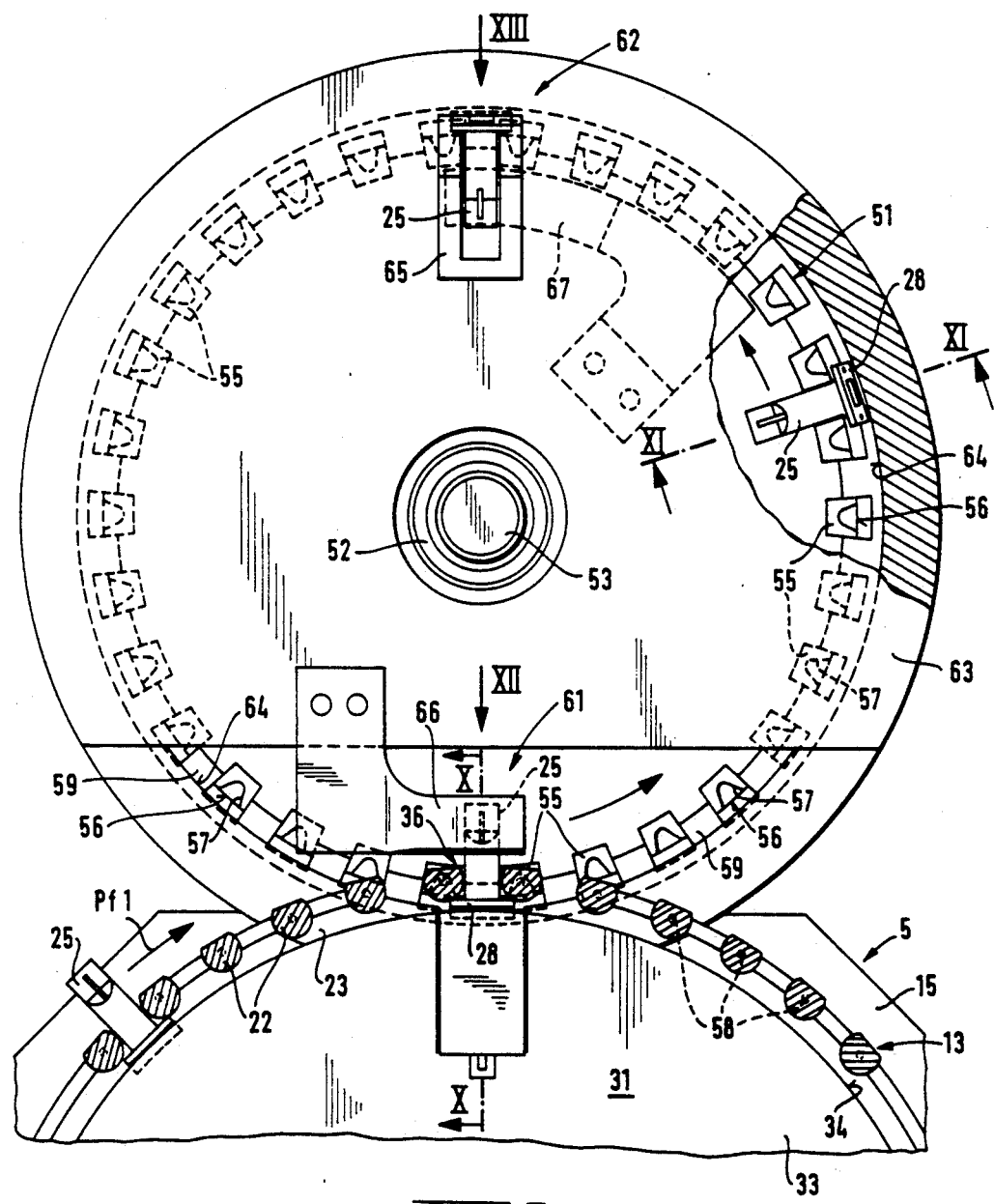
FIG. 9 is a section along line IX—IX in FIG. 8.

The rotating wheel 51 is rotatably supported by ball bearings 52 on a spigot 53 which is attached via an arm 54 to the stator plate 15 (FIG. 8). The rotating wheel 51 has an essentially disk-like form and, on its radial external edge, has teeth 55 directed against the free ends of rods 22, with the teeth spacing being equal to the spacing of the rods.

The teeth 55 have an external surface contour 56 and width arranged such that they form an extension of the cuvette guide formed by rods 22 in the delivery region (window 36).

The teeth 55 are provided with frontal and externally radiating open recesses 57 in which pins 58, projecting from the free ends of the rods 22, can engage in the manner of a gear.

The rotating wheel 51 thus is coupled with the rotor 13 such that the space 23 in the delivery area 36 is aligned with spaces 59 of two adjacent teeth 55 of the rotating wheel 51.

The free front sides of the tooth construction 55 are covered by a fixed plate 63 up to the feed or delivery site 61, 62, whereby cuvettes 25 present in the rotating wheel 51 are protected from axial fall out. Plate 63 has the form of a pot and is positioned around the outer peripheral rim of the rotating wheel 51, whereby the cuvettes can stay on the inner peripheral rim and are protected against radial fall out (FIG. 11).

Figure 12:
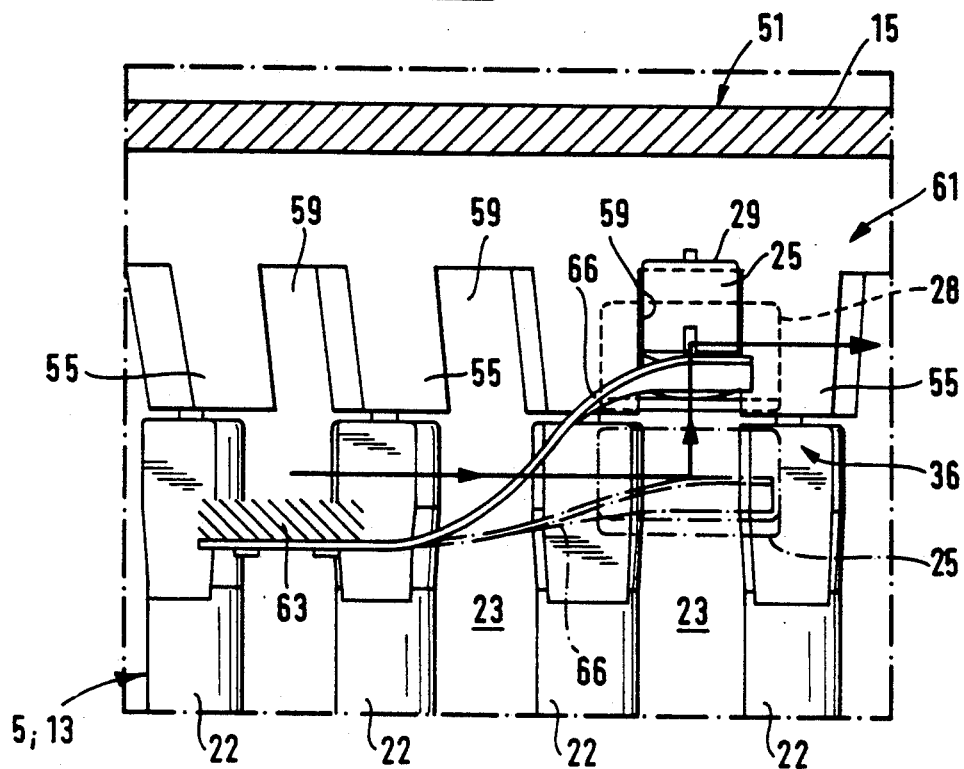

A charge spring 66 pushes the cuvettes 25, which have been transported from the aligning and separating device 5, into the delivery area 36 in the lower region of the rotating wheel 51, into the space 59 between two adjacent teeth 55 (FIG. 12).

Figure 13:
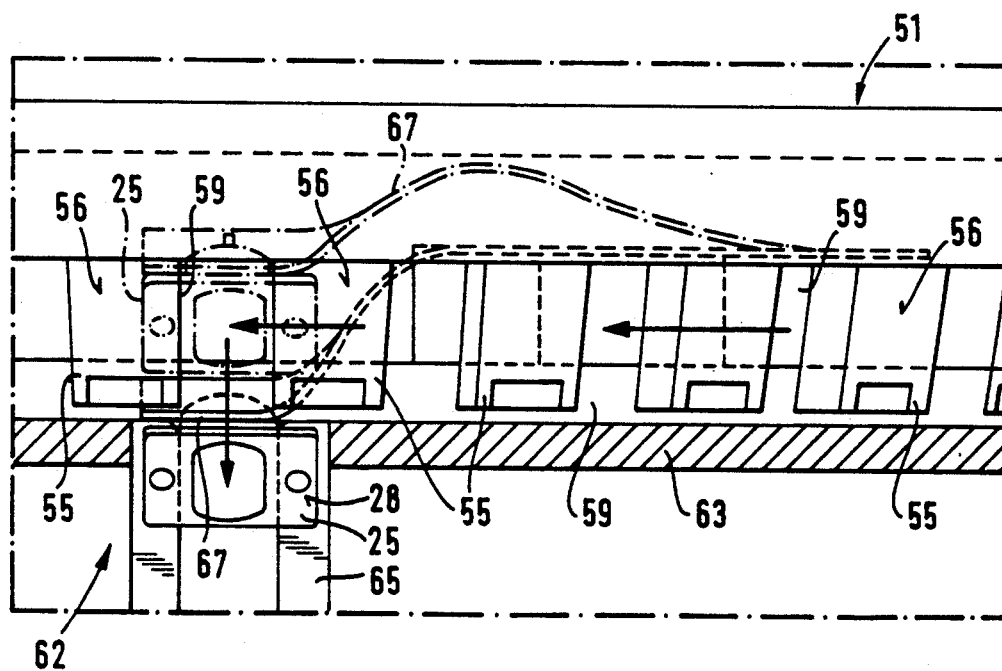

In an upper position of the rotating wheel 51, the cuvettes 25 are expelled by means of a delivery spring and are pushed into a cuvette store 65 (FIG. 13). From there the cuvettes 25 are transported to their destination in the analytical instrument.

The invention has been described with reference to specifically preferred embodiments. Additional embodiments within the skill of an artisan and spirit of the invention are contemplated and intended to be included within the inventive concept.

I claim:

1. An apparatus for separating a plurality of cuvettes supplied in bulk form to an analytical instrument, the cuvettes being suitable for the performance of photometric measurements on samples contained in the cuvettes, and each cuvette being made in one piece from light-transmitting plastic and having a tubular body with two plane-parallel walls, and each plane-parallel wall having a flange attachment which extends outwards and at right angles to the plane-parallel walls, the flange attachments of the two plane-parallel walls being symmetrical with one another relative to the longitudinal axis of the cuvette, which apparatus comprises:

a) a receiving station for receiving cuvettes;
b) a device for separating the cuvettes, said device having an inlet through which the cuvettes are inserted into the device and an outlet through which the individual cuvettes successively leave the device, said device having:
  i) a base plate;
  ii) a fixed plate mounted on the base plate and disposed at a predetermined angle to a vertical line;
  iii) a bearing rod mounted on the fixed plate and disposed at right angles thereto, the bearing rod being inclined at a predetermined angle to a horizontal line;
  iv) a rotatable disc rotatably mounted on the bearing rod and disposed parallel to the fixed plate, said disc having a peripheral edge;
  v) a cylindrical arrangement of a plurality of equal-sized rods having two ends, the rods being equally spaced from each other around a circumference concentric with the bearing rod, the rods being aligned parallel to the bearing rod and inclined at the same angle to a horizontal line as is the bearing rod, one end of each rod being permanently secured to the rotatable disc and the other end of the rod being free and separated from the fixed plate by a predetermined gap, and the distance between adjacent rods being just sufficient for the tubular body of the cuvette to enter between the adjacent cylindrical rods when the plane-parallel walls of the cuvette are parallel to the longitudinal axis of the rods, said fixed plate, rods and rotatable disc forming a cage-like structure;
  vi) motor-driven means for rotating the rotatable disc at a predetermined speed;
  vii) a fixed annular disc mounted on the fixed plate and having a central aperture for receiving the bearing rod, the peripheral edge of the disc being configured and dimensioned to be inside the arrangement of rods, and the distance between the rods and the peripheral edge of the fixed annular disc being slightly greater than the thickness of the flange attachment on the cuvettes; and viii) a first opening in the fixed plate, positioned above the lowest portion of the fixed annular disc with respect to the vertical line of the fixed annular disc, the opening serving as the inlet for inserting cuvettes; and c) means for conveying cuvettes from the receiving station to the inlet of the device.

2. The apparatus of claim 1, wherein the device for separating the cuvettes further comprises:

i) a second opening in the fixed plate, positioned generally at the lowest portion of the fixed annular disc with respect to a verticle line, the opening serving as an outlet for discharging individual cuvettes when their flange attachments come to rest between the arrangement of rods and the peripheral edge of the fixed annular disc during rotation of the cage-like structure; and ii) means for delivering individual cuvettes through the second opening in the fixed plate, when the cuvette is in front of the second opening during rotation of the cage-like structure.

3. The apparatus of claim 1, wherein the device for separating cuvettes further comprises:

i) a second opening in the fixed plate, positioned generally at the highest portion of the fixed annular disc with respect to a verticle line, the opening serving as an outlet for discharging individual cuvettes when their flange attachments come to rest between the arrangement of rods and the peripheral edge of the fixed annular disc during rotation of the cage-like structure; and ii) means for delivering individual cuvettes through the second opening in the fixed plate, when the cuvette is in front of the second opening during rotation of the cage-like structure.

4. The apparatus of claim 2, wherein the angle of inclination of the rods relative to a horizontal line is between about 10 and about 20 degrees.

5. The apparatus of claim 3, wherein the angle of inclination of the rods relative to a horizontal line is between about 10 and about 20 degrees.

6. The apparatus according to claim 2, wherein the angle of inclination of the rods relative to a horizontal line is about 15 degrees.

7. The apparatus according to claim 3, wherein the angle of inclination of the rods relative to a horizontal line is about 15 degrees.

8. An apparatus according to claim 2, wherein the motordriven means for rotating the rotatable disk has a speed between about 8 and about 15 revolutions per minute.

9. An apparatus according to claim 3, wherein the motordriven means for rotating the rotatable disk has a speed between about 8 and about 15 revolutions per minute.

10. The apparatus of claim 2, wherein the motor-driven means for rotating the rotatable disc has a speed of about 11 revolutions per minute.

11. The apparatus of claim 3, wherein the motor-driven means for rotating the rotatable disc has a speed of about 11 revolutions per minute.

12. An apparatus for separating a plurality of cuvettes supplied in bulk form to an analytical instrument, the cuvettes being suitable for the performance of photometric measurements on samples contained in the cuvettes, and each cuvette being made in one piece from light-transmitting plastic and having a tubular body with two plane-parallel walls, and each plane-parallel wall having a flange attachment which extends outwards and at right angles of the plane-parallel walls, the flange attachments of the two plane-parallel walls being symmetrical with one another relative to the longitudinal axis of the cuvette, which apparatus comprises:

a) a base plate;

b) a fixed plate mounted on the base plate and disposed at a pre-determined angle to a vertical line;

c) a bearing rod mounted on the fixed plate and disposed at right angles thereto, the bearing rod being inclined at a predetermined angle to a horizontal line;

d) a rotatable disc rotatably mounted on the bearing rod and disposed parallel to the fixed plate, said disc having a peripheral edge;

e) a cylindrical arrangement of a plurality of equal-sized rods having two ends, the rods being equally spaced from each other around a circumference concentric with the bearing rod, the rods being aligned parallel to the bearing rod and inclined at the same angle to a horizontal line as is the bearing rod, one end of each rod being permanently secured to the rotatable disc and the other end of the rod being free and separated from the fixed plate by a predetermined gap, and the distance between adjacent rods being just sufficient for the tubular body of the cuvette to enter between the adjacent cylindrical rods when the plane-parallel walls of the cuvette are parallel to the longitudinal axis of the rods, said fixed plate, rods and rotatable disc forming a cage-like structure;

f) motor-driven means for rotating the rotatable disc at a predetermined speed;

g) a fixed annular disc mounted on the fixed plate and having a central aperture for receiving the bearing rod, the peripheral edge of the disc being configured and dimensioned to be inside the arrangement of rods, and the distance between the rods and the peripheral edge of the fixed annular disc being slightly greater than the thickness of the flange attachment on the cuvettes; and h) a first opening in the fixed plate, positioned above the lowest portion of the fixed annular disc with respect to the vertical line of the fixed annular disc, the opening serving as an inlet for inserting cuvettes.

* * * * *